(12) United States Patent
Santos et al.

(10) Patent No.: US 11,906,688 B2
(45) Date of Patent: Feb. 20, 2024

(54) USING ELECTRICAL SIGNAL AS A MEASURE OF WATER WETTABILITY FOR DIRECT EMULSION FLUIDS

(71) Applicant: Halliburton Energy Services, Inc., Houston, TX (US)

(72) Inventors: Catherine Martin Santos, Houston, TX (US); Jeffrey James Miller, Spring, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 940 days.

(21) Appl. No.: 16/594,835

(22) Filed: Oct. 7, 2019

(65) Prior Publication Data
US 2021/0103070 A1 Apr. 8, 2021

(51) Int. Cl.
| | | |
|---|---|---|
| *G01V 3/24* | (2006.01) | |
| *E21B 21/01* | (2006.01) | |
| *G01N 27/00* | (2006.01) | |
| *G01N 33/28* | (2006.01) | |

(52) U.S. Cl.
CPC .......... *G01V 3/24* (2013.01); *E21B 21/01* (2013.01); *G01N 27/00* (2013.01); *G01N 33/2823* (2013.01)

(58) Field of Classification Search
CPC ......... Y02P 10/20; E21B 21/01; G01N 27/00; G01N 33/2823; G01N 27/605; G01V 3/24
See application file for complete search history.

(56) References Cited

U.S. PATENT DOCUMENTS

| | | | |
|---|---|---|---|
| 6,740,216 B2 | 5/2004 | Diakonov | |
| 7,679,992 B2 | 3/2010 | Chen | |
| 9,359,881 B2 | 6/2016 | DiSantis | |
| 2002/0061823 A1 | 5/2002 | Schlemmer et al. | |
| 2003/0206024 A1 | 11/2003 | Murphy, Jr. et al. | |
| 2008/0159073 A1* | 7/2008 | Chen | G01V 3/265 367/25 |
| 2010/0042335 A1* | 2/2010 | Murphy | G01N 33/2823 702/30 |
| 2010/0283492 A1 | 11/2010 | Growcock et al. | |
| 2012/0229135 A1 | 9/2012 | Hurlimann | |
| 2013/0068459 A1* | 3/2013 | Kippie | C09K 8/575 166/278 |
| 2015/0316527 A1 | 11/2015 | Stock et al. | |
| 2016/0024906 A1 | 1/2016 | Jamison et al. | |
| 2016/0152885 A1* | 6/2016 | Offenbacher | C09K 8/57 166/305.1 |
| 2016/0222274 A1* | 8/2016 | Hoskins | C09K 8/516 |
| 2020/0339859 A1* | 10/2020 | Santos | E21B 21/065 |

OTHER PUBLICATIONS

International Search Report and Written Opinion for Application No. PCT/US2019/055399, dated Jul. 6, 2020.
"Successful Application of Direct Emulsion Fluid in Oklahoma Shale and the Delaware Basin" Harton et al, 2018 American Association of Drilling Engineers.

* cited by examiner

*Primary Examiner* — Alvaro E Fortich
*Assistant Examiner* — Adam S Clarke
(74) *Attorney, Agent, or Firm* — Thomas Rooney; C. Tumey Law Group PLLC (57) ABSTRACT

A method of determining wettability may include: measuring an electrical property of a drilling fluid; and correlating the electrical property to wettability.

19 Claims, 2 Drawing Sheets

USING ELECTRICAL SIGNAL AS A MEASURE OF WATER WETTABILITY FOR DIRECT EMULSION FLUIDS

BACKGROUND

The Electrical Stability meter (ES meter) is conductivity measurement device has been used to characterize invert emulsion drilling fluids, also known as oil-based drilling fluids, or oil-external drilling fluids in the oil and gas industry. In invert emulsion drilling fluids, water droplets are dispersed within a continuous oil phase which may be stabilized by the addition of emulsifiers. The water phase is usually about 5% to about 40% of the total liquid volume and usually includes brines such as calcium chloride brine. The brine concentration is adjusted to control the water exchange between the drilling fluid and the formation being drilled and to aid in formation stability. If the formulation of the invert emulsion drilling fluid becomes unbalanced, due to contamination, improper product additions, or thermal degradation for example, the emulsion can flip. When such flipping happens, the water becomes the continuous phase, which may cause the solids in the drilling fluid to become water wet. There may be undesirable side effects when an emulsion flips which may require remediation. ES meters may be used to determine an ES voltage of a drilling fluid which may be correlated to the stability of the emulsion. The higher the ES voltage measured for the invert emulsion drilling fluid, the stronger the emulsion created.

An ES meter may be used to carry out an electrical stability test method as specified by the American Petroleum Institute (API) in "Recommended Practice Standard Procedure for Field Testing Oil-Based Drilling Fluids", API Recommended Practice 13B-2, Fifth Edition, April 2014. The API defines electrical stability (ES) of an oil-based drilling fluid mud is a property related to its emulsion stability and oil-wetting capability. Oils are typically non-conductive as oils generally do not contain ions capable of carrying electrical charge. ES is determined by applying a voltage-ramped, sinusoidal electrical signal across a pair of parallel flat-plate electrodes immersed in the oil-based drilling fluid. The current flowing between the electrodes remains low until a threshold voltage is reached, whereupon the current rises very rapidly. This threshold voltage is referred to as the ES of the oil-based drilling and is defined as the voltage in peak volts-measured when the current reaches 61 µA. This API Procedure also specifies instrument parameters that should be controlled to make repeatable measurements. Such parameters include the waveform, AC frequency (340±10 Hz), voltage ramp rate, break current, electrode diameter, and gap spacing, for example.

The strong electric field induced by the ES meter causes dispersed water droplets in the drilling fluid to orient and coalesce to form conductive bridges between the faces of the electrodes of the ES meter probe. Solid materials in the drilling fluid may aid or interfere with formation of the conductive bridge. These solid materials typically include, for example, weight material that is added to increase the density, drill cuttings or drilled formation solids, and colloidal solids added to control the viscosity and suspension properties of the drilling fluid. Through ES testing a stability of the emulsion may be determined. In general, a higher ES measurement indicates a larger current required to cause the dispersed water to coalesce to conductive bridges indicating a stronger emulsion is formed In water based drilling fluids, also known as direct emulsion drilling fluids, the continuous phase is water and the discontinuous phase is oil. Unlike invert emulsions, direct emulsion drilling fluids are not typically tested for emulsion stability using the ES meter method since the water based drilling fluids are typically conductive due to the presence of dissolved ions in the aqueous phase.

In addition to qualifying whether the drilling fluid is an oil based (invert) emulsion or a water based (direct) emulsion, another quality of a drilling fluid that is often tested and designed for is wettability. Tests for measuring wettability for a drilling fluid are typically qualitative. A typical wettability test may include preparing the drilling fluid and thereafter dropping a few drops of the drilling fluid are onto a water surface. A direct emulsion drilling fluid is determined as water wet if the drops disperse in the water, otherwise the direct emulsion drilling fluid is termed as oil wet. The qualitative test for wettability may be unreliable as the test may be reliant on the skill and consistency of the person performing the test.

BRIEF DESCRIPTION OF THE DRAWINGS

These drawings illustrate certain aspects of some of the present disclosure and should not be used to limit or define the disclosure.

DETAILED DESCRIPTION

Disclosed herein are apparatus, systems, and methods for determining wettability of direct emulsion drilling fluids. The apparatus, systems, and methods described herein may include utilizing an electrical measurement device to generate an electrical measurement and correlating the electrical measurement to wettability of the drilling fluid. Some electrical measurement devices, may include, without limitation, ES meters, spacer fluid wettability testers, volt meters, ammeters, and ohmmeters, for example. Correlation of the electrical measurement to wettability may be done by any methods such as by a calibration curve or by a correlating function, for example. An example method utilizing an ES meter to determine wettability will be described in detail below.

The circuitry of the ES meter performs six primary functions: power supply, test control, high voltage ramping AC sine wave generation, voltage measurement, break current threshold detection, and ES voltage display. In some examples, the ES meter may be configured to output a signal corresponding to the measured voltage also known as the ES. The output signal may be sent for further processing or analysis over a wired to wireless connection to a computer system. The sine wave generated by the ES meter generally starts at zero volts and increases, or ramps, at a steady rate. The ramping AC voltage is applied to the direct emulsion drilling fluid to be tested by means of a probe immersed in the direct emulsion drilling fluid. The probe geometry may be defined by in API Recommended Practice 13B-2 discussed above. The probe typically contains two electrodes separated by a gap of pre-defined width and embedded in the electrically insulating body of the probe. There may be different probe geometries depending on the end user and which standards are being followed for a particular ES test. Typically, the probes specified by the API are flat, 0.125 inches in diameter, and separated by a 0.061-inch gap. When the probe is immersed in the drilling fluid, the gap is filled with the fluid.

Figure 1:
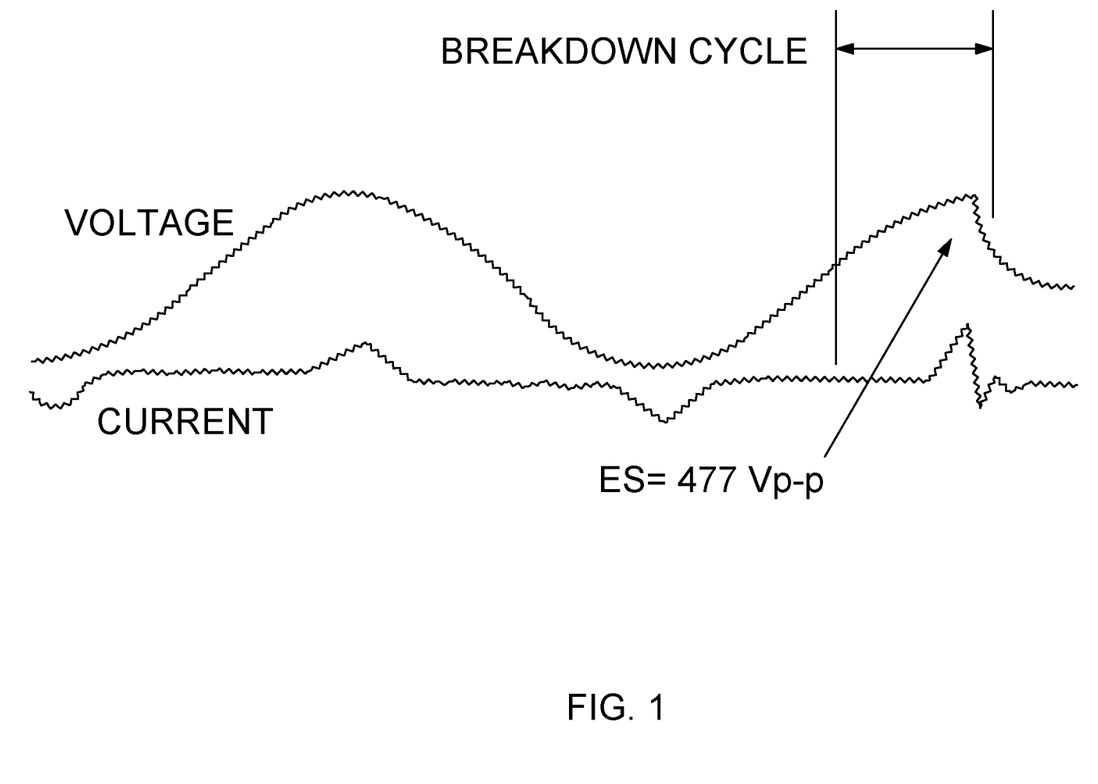
FIG. 1 is an illustration of a waveform output from an ES meter.

ES testing may be performed by submerging a probe into a direct emulsion drilling fluid and selecting a breakdown current where the direct emulsion drilling fluid is said to be conductive. The breakdown current may be defined by testing specifications such as those published by the API or may be selected by an operator for a particular application. In some examples, the breakdown current may be at least 1 µA to about 1000 µA. Alternatively, the breakdown current may selected from a point in a range of about 1 µA to about 100 µA, about 100 µA to about 300 µA, about 300 µA to about 700 µA, or about 700 µA to about 1000 µA. The breakdown current used in ES testing procedures published in API Recommended Practice 13B-2, Fifth Edition, April 2014 is 61 µA. A ramping AC current is then applied through a first probe and the current is transmitted through the direct emulsion drilling fluid to a second probe. The current flowing through the drilling fluid may then be measured from the current at the second probe. The ES value or ES voltage of the drilling fluid may be the voltage where the measured current at the second probe equals the selected breakdown current. FIG. 1 is an illustration of a waveform output from an ES meter. In FIG. 1, of a typical breakdown cycle in a drilling fluid is shown. In FIG. 1, the current is almost flat until immediately prior to breakdown, then the current rises sharply. The voltage where the current rises above the breakdown current is the ES voltage indicated by the breakdown cycle in FIG. 1.

As mentioned above, direct emulsion drilling fluids are conductive due to the water continuous external phase. The aqueous phase typically contains dissolved ions which facilitate charge carrying and contribute to conductivity of the direct emulsion drilling fluid. A measured ES voltage of a direct emulsion drilling fluid may be expected to be relatively lower than for a invert emulsion drilling fluid where the continuous phase is a less conductive oil. While the measured ES voltage of a direct emulsion drilling fluid may be a poor indicator of emulsion stability, the ES voltage measurement may be correlated to wettability of the fluid and, more specifically, whether the direct emulsion drilling fluid is water wet or oil wet. As discussed above the current methods for determining wettability of direct emulsion drilling fluids includes qualitative measurements and there may be a degree of subjectivity to the results of the wettability test. Correlating ES voltage to wettability in a quantitative manner may have several advantages over qualitative testing currently used.

A method of determining wettability of direct emulsion drilling fluids may be to select a breakdown current, perform ES testing using an ES testing meter to determine the ES voltage at the breakdown current, and correlating the ES voltage to wettability at the breakdown current. As ES voltage is a function of the selected breakdown current, the ES voltage may be higher if a selected breakdown current is relatively higher. Similarly, the ES voltage may be lower if the selected breakdown current is relatively lower. For these reasons, correlating the wettability to ES voltage may be dependent on the selected breakdown current. A calibration curve may be one kind of correlation between ES voltage and wettability that may be generated for a breakdown current. A calibration curve may be used to reference a measured ES voltage to a wettability. Another correlation may be a mathematical function that converts the ES voltage to wettability.

The method of correlating the ES voltage of a direct emulsion drilling fluid to wettability will now be explained in more detail with reference to Tables 1 and 2. Tables 1 and 2 illustrate direct emulsion drilling (water external phase) fluids prepared with 45/55 oil-to-water volume ratio in Table 1 and with 55/45 oil-to-water volume ratio in Table 2. Each of the fluids were prepared with brine, sodium carbonate, xanthan gum, pH buffer, a filtration control additive, an emulsifier, and a viscosifier. The fluids were prepared and hot rolled at 120° F. (49° C.). After hot rolling, the ES voltage of each sample was tested using a Fann® Electrical Stability Tester (EST) using the default 61 µA breakdown current setting. A qualitative wettability test was also performed on each of the fluids by placing a few drops of the fluid in water and observing the dispersion of the fluid to qualitatively determine wetness. It was observed that the direct emulsion drilling fluids which were water wet and those that were oil wet displayed disparate ES voltages. Water wet direct emulsion drilling fluids from Tables 1 and 2 each have an ES voltage of less than about 10 volts. Oil wet direct emulsion drilling fluids from Tables 1 and 2 each have an ES voltage of greater than about 20 volts. Thus, the ES voltage of a direct emulsion drilling fluid can be correlated to the wettability of the direct emulsion drilling fluid. For a breakdown current of 61 µA, direct emulsion drilling fluids which are water wet have a measured ES voltage of about 10 volts or less and direct emulsion drilling fluids which are oil wet have a measured ES voltage of about 20 volts or greater. It was observed that the correlation between measure ES voltage and wettability held for fluids prepared with 45/55 oil-to-water volume ratio and fluids prepared with 55/45 oil-to-water volume ratio.

TABLE 1

| | 45/55 Volume Oil-to-Water | | | | | | | | |
|---|---|---|---|---|---|---|---|---|---|
| | 1 | 2 | 3 | 4 | 5 | 6 | 7 | 8 | 9 |
| 10 ppg NaCl Brine, lb/bbl | 230 | 230 | 230 | 230 | 230 | 230 | 230 | 230 | 230 |
| Sodium Carbonate | 0.2 | 0.2 | 0.2 | 0.2 | 0.2 | 0.2 | 0.2 | 0.2 | 0.2 |
| Xanthan Gum | 0.75 | 0.75 | 0.5 | 0.5 | 0.25 | 0.25 | 1 | 0.25 | 1 |
| pH Buffer | 1.25 | 1.25 | 1.25 | 1.25 | 1.25 | 1.25 | 1.25 | 1.25 | 1.25 |
| Filtration Control | 2 | 2 | 2 | 2 | 2 | 2 | 2 | 2 | 2 |
| Emulsifier | 4 | 3 | 3.5 | 2 | 3 | 4 | 5 | 5 | 2 |
| Viscosifier | 10 | 10 | 8 | 8 | 8 | 8 | 8 | 8 | 8 |
| Diesel lb/bbl | 130.2 | 130.2 | 130.2 | 130.2 | 130.2 | 130.2 | 130.2 | 130.2 | 130.2 |
| ES | 4 | 4 | 4 | 3 | 2 | 30 | 2 | 47 | 2 |
| Wettability (Qualitative) | Water Wet | Water Wet | Water Wet | Water Wet | Water Wet | Oil Wet | Water Wet | Oil Wet | Water Wet |

TABLE 2

55/45 Volume Oil-to-Water

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 10 ppg NaCl Brine, lb/bbl | 184.6 | 184.6 | 184.6 | 184.6 | 184.6 | 184.6 | 184.6 | 184.6 | 184.6 | 184.6 | 184.6 | 184.6 | 184.6 | 184.6 |
| Sodium Carbonate | 0.2 | 0.2 | 0.2 | 0.2 | 0.2 | 0.2 | 0.2 | 0.2 | 0.2 | 0.2 | 0.2 | 0.2 | 0.2 | 0.2 |
| Xanthan Gum | 1 | 0.5 | 0.75 | 0.25 | 0.25 | 0.5 | 0.4 | 0.4 | 0.25 | 0.4 | 0.3 | 0.3 | 0.5 | 0.3 |
| pH Buffer | 1.25 | 1.25 | 1.25 | 1.25 | 1.25 | 1.25 | 1.25 | 1.25 | 1.25 | 1.25 | 1.25 | 1.25 | 1.25 | 1.25 |
| Filtration Control | 2 | 2 | 2 | 2 | 2 | 2 | 2 | 2 | 2 | 2 | 2 | 2 | 2 | 2 |
| Emulsifier | 5 | 3.5 | 3 | 3 | 1.5 | 2.5 | 2.5 | 2.5 | 3 | 3 | 2.5 | 2.5 | 5 | 4 |
| Viscosifier | 10 | 8 | 10 | 8 | 8 | 8 | 8 | 8 | 8 | 8 | 8 | 8 | 8 | 8 |
| Diesel lb/bbl | 157.35 | 157.35 | 157.35 | 157.35 | 157.35 | 157.35 | 157.35 | 157.35 | 157.35 | 157.35 | 157.35 | 157.35 | 157.35 | 157.35 |
| ES | 8 | 3 | 3 | 63 | 2 | 2 | 1 | 4 | 37 | 9 | 8 | 3 | 43 | 35 |
| Wettability (Qualitative) | Water Wet | Water Wet | Water Wet | Oil Wet | Water Wet | Water Wet | Water Wet | Water Wet | Oil Wet | Water Wet | Water Wet | Water Wet | Oil Wet | Oil Wet |

Although only ES meters have been discussed so far, any other suitable electrical measurement equipment may be used to generate an electrical measurement which may be correlated with wettability. For example, cement spacer testing methods outlined API RP (recommended practice) 10B-2 2nd Edition, April 2013 outlines methods for testing wettability of spacer fluids, pre-flush fluids, and spacer/surfactant fluids combinations. The methods utilize a cement wettability tester which includes a test container, a mixing mechanism, and control equipment which provides power and measures an electrical current through the tested fluid. Normally, oil-external spacer are not electrically conductive, while water-based spacers are. Actual conductivity depends on the solution chemistry of the fluid which may change as the fluid is sheared and heated. The control equipment measures the electrical activity in the tested fluid and on the electrode surfaces and provides a continuous reading that reflects the apparent wettability. When the test container is empty, no electrical activity is present and the reading should be 0 Hn (Hogans, a dimensionless unit). When the test cup is full of a stable, invert emulsion oil-external drilling fluid, the reading should also be 0 Hn as there is little to no current flowing through the oil-external drilling fluid. The oil-external drilling fluid may be subjected to heat and shear which may cause changes in the external phase such that the external phase exhibits measurable electrical activity. The electrical activity may then be correlated to an apparent wettability. Similarly, an aqueous-external direct emulsion drilling fluid may be tested which may have measurable electrical activity, which may be correlated to wettability, before shear and heating. Shearing and heating may alter the external phase such that the electrical activity of the direct emulsion drilling fluid is altered. Electrical measurements taken during the shearing and heating may be correlated to wettability such that wettability as a function of temperature and shear may be calculated. Other electrical measurement equipment may include, but is not limited to, volt meters, ammeters, and ohmmeters, for example. The output of each of the measurement equipment may be correlated to wettability using a calibration curve, for example.

A wettability correlation may be used to determine the wettability condition of a direct emulsion drilling based least in part on an electrical measurement of the drilling fluid. For example, a wettability condition may be water-wet, oil-wet, or intermediate wettability. Once the wettability of a direct emulsion drilling fluid is determined, additional steps may be taken to treat or divert the direct emulsion drilling fluid such that the direct emulsion drilling fluid remains water-wet. As discussed above, wettability may be an important property of drilling fluids and may have impacts on drilling operations when wettability is modified. In some examples when a drilling fluid which is originally water wet flips to become oil wet during a drilling operation, formation damage may occur. Techniques described herein may allow for monitoring of the drilling fluid wettability which may indicate if intervention is required to maintain the desired wettability of a drilling fluid. The methods for determining whether a direct emulsion drilling fluid is water wet or oil wet may be applied in a laboratory or mud plant applications or may be performed in real time at a drilling rig for example. Electrical equipment capable of measuring an electrical property of a direct emulsion drilling fluid may be provided, and an output thereof may be correlated to wettability. An analysis of the wettability may indicate that the drilling fluid requires intervention to maintain a water-wet state.

The method of correlating the cement wettability tester current output of a direct emulsion drilling fluid to wettability will now be explained in more detail with reference to Tables 3 and 4. Tables 3 and 4 illustrate direct emulsion drilling (water external phase) fluids prepared with 50/50 oil-to-water volume ratio in Table 3 and with 60/40 oil-to-water volume ratio in Table 4. Each of the fluids were prepared with brine, xanthan gum, pH buffer, an emulsifier, and a viscosifier. The fluids in Table 3 were prepared and hot rolled at 150° F. (65° C.). After hot rolling, the ES voltage and qualitative wettability of each sample was tested at 150° F. (65° C.) using a Fann® Electrical Stability Tester (EST) using the default 61 µA breakdown current setting. It was observed that the direct emulsion drilling fluids which were water wet and those that were oil wet again displayed disparate ES voltages. Water wet direct emulsion drilling fluids from Table 3 each have an ES voltage of less than about 10 volts. Oil wet direct emulsion drilling fluids from Table 3 have an ES voltage of greater than about 20 volts. Thus, the ES voltage of these direct emulsion drilling fluids can be correlated to the wettability as before. By measuring the ES at varied test temperatures, some differences were were observed. For example, Sample 18 indicated an ES value of 6 at 150° F. (65° C.), while the reading at ambient temperature was 1. The direct emulsion drilling fluids were then placed in a Fann Model C1001 Wettability Tester. Its electrical signal amplification was pre-set at 175 microamperes for 10 ppg NaCl brine to represent the water wet continuous phase signal. It was observed that sample 15, an oil-wet fluid, indicated zero electrical activity initially after placing the sample into the mixing container. The signal remained zero even while applying shear to the mixer. While mixing, treatments were added to sample 15 in order to attempt to achieve a water-wet state. A volume of 2 cubic centimeters of Surfactant B was added to this sample and allowed to mix thoroughly. The mixing container was programmed to heat up to 120° F. (49° C.). As heating/mixing was in progress, a current reading of 25-80 was observed briefly at 103° F. (39.5° C.). The reading reverted to zero as the temperature increased up to the setpoint. A second volume of 2 cubic centimeters of Surfactant B was added to the sample with no apparent change in the reading or wettability. Finally, 60 cubic centimeters of NaCl brine was added to the sample which caused an immediate signal increase to a reading of 180 microamperes. Sample 15 was mixed for three additional minutes before concluding the test and measuring the corresponding ES of 2.

The water wet fluids (16, 17, 18) all displayed significantly higher electrical current, with initial values ranging from 140 to 160 microamperes. While mixing, these samples achieved the full electrical current expected of the continuous brine phase. The use of the Model C1001 allowed for further evaluation of additional variables with continuous current readout to simulate various conditions which fluids may encounter in a circulating system. Monitoring of the electrical signal allowed for a correlation between measured current and wettability, and this held for fluids prepared with the 50/50 oil-to-water volume ratio.

The fluids in Table 4 were mixed and then tested immediately afterward. The ES voltage and qualitative wettability of each sample was tested using a Fann® Electrical Stability Tester (EST) using the default 61 µA breakdown current setting, and the Fann Model C1001 Wettability Tester was used to measure electrical current with signal amplification pre-set at 180 microamperes for 10 ppg NaCl brine. After recording the initial readings, the mixing container was heated to 120° F. (49° C.) with continuous mixing and monitoring of the current readings. As the stable readings of 175-185 indicated highly conductive water-wet direct emulsion fluids, two methods were used to stress the fluids and attempt to disrupt their water-wet condition. For sample 20, an invert emulsifier consisting of modified tall oil fatty acids was added to the sample to disrupt the direct emulsion. The addition of up to 2 cubic centimeters invert emulsifier did not cause any changes to the current readings or condition of the sample. When this was increased to a total of 3 cc invert emulsifier, the current rapidly dropped from 180 to 20 microamperes, and over the next 30 seconds it continued to decrease to 15, 10, and 5 microamperes. At this point a break in the viscosity of the emulsion was observed, and the current dropped to 0 indicating an oil-wet condition. When mixing was stopped, the sample had a rapid phase separation and this caused the lower brine phase to contact the electrodes. This resulted in a reading of 140. Diesel was observed on surface with an initial ES reading of 11 (clean diesel is typically greater than 1000), and brine on the bottom layer indicated an ES of 1 or 2.

For sample 19, the direct emulsion was heated as before, and additional diesel was added to stress the emulsion. The fluid was diluted stepwise with 100 and then 50 cubic centimeters of additional diesel, representing a full addition of 150 cubic centimeters and a new oil-to-water volume ratio of approximately 70/30. This ratio is typical of invert emulsion formulations. The current was maintained at 175 throughout the additions, indicating a stable water-wet state while mixing even with a high volume fraction of diesel. As with sample 20, the invert emulsifier was added as a second step to simulate either contamination, improper treatment, or dosing in attempt to convert the direct emulsion system to an oil-wet invert emulsion. Addition of 0.5 cc oil-wetting emulsifier did not change the wettability, as the observed reading of 175 remained steady. However, as the emulsifier was slowly increased to 0.9 cc, a very rapid drop in electrical signal (to 0) and a simultaneous break in the viscosity was observed. Monitoring of the electrical signal allowed for a more immediate correlation between measured current and wettability, and this held for fluids prepared 60/40 oil-to-water volume ratios and those with higher oil content. As these results suggest, multiple sets of electrodes can also allow for monitoring of phase separation or system contamination/heterogeneity.

TABLE 3

| | 50/50 Volume Oil-to-Water | | | |
|---|---|---|---|---|
| | 15 | 16 | 17 | 18 |
| 10 ppg NaCl Brine, lb/bbl | 209.5 | 209.5 | 209.5 | 209.5 |
| Xanthan Gum | 0.4 | 0.4 | 0.4 | 0.4 |
| pH Buffer | 1.3 | 1.3 | 1.3 | 1.3 |
| Emulsifier A | 4 | 0 | 0 | 0 |
| Emulsifier B | 0 | 0.55 | 2 | 4 |
| Viscosifier | 8 | 8 | 8 | 8 |
| Diesel lb/bbl | 147 | 147 | 147 | 147 |
| ES at 150° F. (65° C.) | 48 | 1 | 1 | 6 |
| Wettability (Qualitative) | Oil Wet | Water Wet | Water Wet | Water Wet |
| ES (after cooling to ambient) | 48 | 1 | 1 | 1 |
| Initial static wettability meter current, microamperes | 0 | 140, variable * | 155 | 160 |
| Final current while shearing sample at 2500 rpm, microamperes | 0 | 180 | 180 | 180 |
| Wettability (Qualitative) | Oil Wet | Water Wet | Water Wet | Water Wet |

* readings ranged between 125 and 140

TABLE 4

| | 60/40 Volume Oil-to-Water | |
|---|---|---|
| | 19 | 20 |
| 10 ppg NaCl Brine, lb/bbl | 191.5 | 191.5 |
| Xanthan Gum | 0.25 | 0.25 |
| pH Buffer | 0.6 | 0.6 |
| Emulsifier B | 2 | 4 |
| Viscosifier | 2 | 2 |

TABLE 4-continued

60/40 Volume Oil-to-Water

| | 19 | 20 |
|---|---|---|
| Diesel lb/bbl | 201.6 | 201.6 |
| ES | 1 | 1 |
| Wettability (Qualitative) | Water Wet | Water Wet |
| Initial static wettability meter current, microamperes | 175 | 180 |
| Current while shearing sample at 1500 rpm and heating to 120° F. (49° C.), microamperes | 175 | 185 |
| Current after adding additional 100 cc diesel | 175 | N/A |
| Current after adding additional 50 cc diesel | 175 | N/A |
| Current after adding oil-wetting emulsifier (cc) | 175 (0.5) | 180 (2) |
| Current after adding oil-wetting emulsifier (cc) | 0 (0.9) | 20-0* (3) |

*readings dropped over 30 seconds

Figure 2:
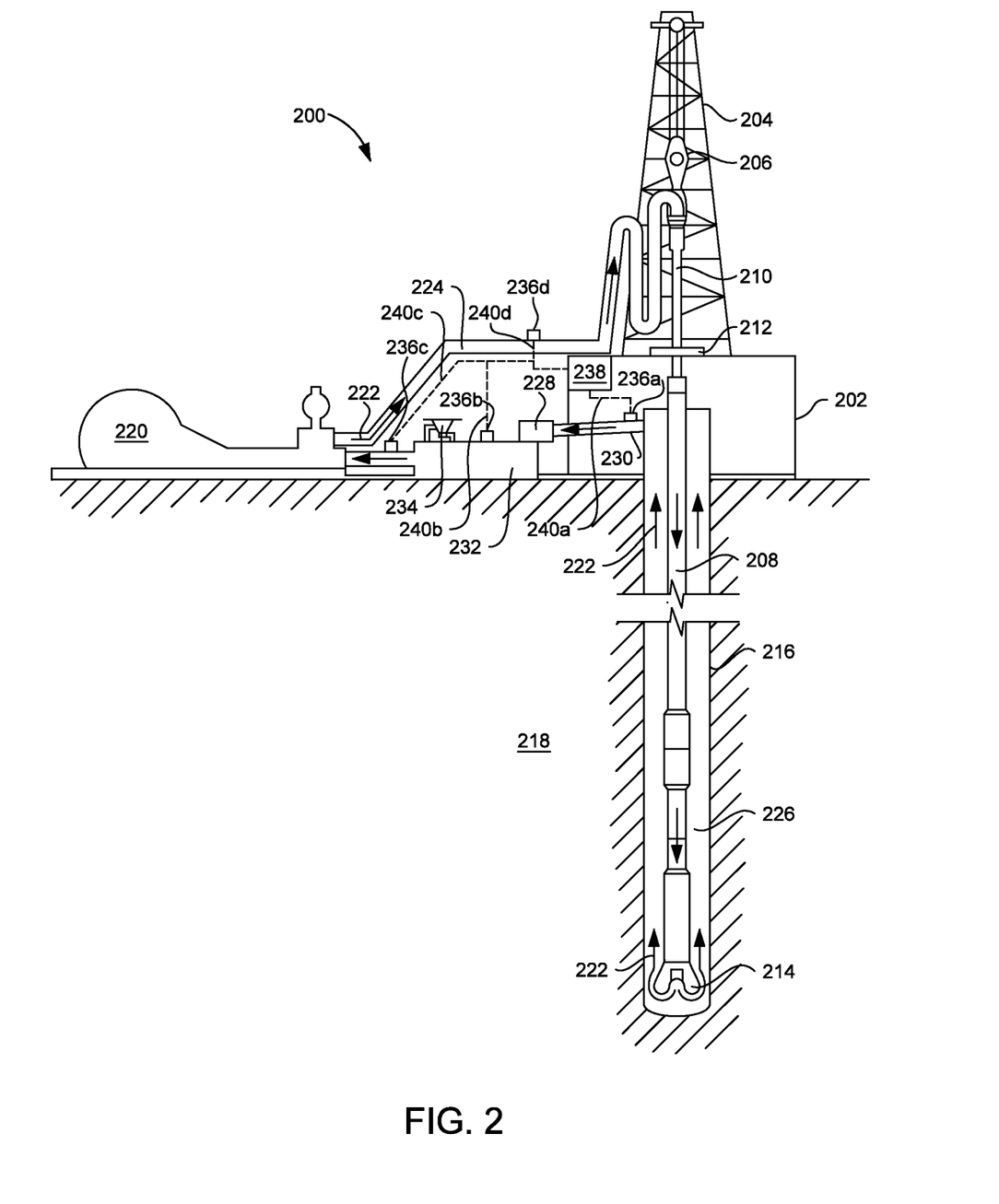
FIG. 2 is a schematic illustration of a drilling rig including electrical signal meters.

Referring now to FIG. 2, illustrated is an exemplary wellbore drilling assembly 200 that may employ one or more electrical meters and, optionally, computing devices described herein in order to monitor a drilling fluid. The electrical meters may be any electrical meters described herein including ES meters, spacer wettability testers, volt meters, ammeters, or ohmmeters, for example. The drilling assembly 200 may include a drilling platform 202 that supports a derrick 204 having a traveling block 206 for raising and lowering a drill string 208. A kelly 210 supports the drill string 208 as it is lowered through a rotary table 212. A drill bit 214 is attached to the distal end of the drill string 208 and is driven either by a downhole motor and/or via rotation of the drill string 208 from the well surface. As the bit 214 rotates, it creates a borehole 216 that penetrates various subterranean formations 218. Although FIG. 2 generally describes a land based drilling operation, the present disclosure is suited to all types of drilling including land based drilling and offshore applications.

A mud pump 220 circulates drilling fluid 222 through a feed pipe 224 and to the kelly 410, which conveys the drilling fluid 222 downhole through an interior conduit defined in the drill string 208 and through one or more orifices in the drill bit 214. The drilling fluid 222 is then circulated back to the surface via an annulus 226 defined between the drill string 208 and the walls of the borehole 216. The drilling fluid 222 serves several purposes, such as providing hydrostatic pressure to prevent formation fluids from entering into the borehole 216 and keeping the drill bit 214 cool and clean during drilling. The drilling fluid 222 also serves to carry drill cuttings and solids out of the borehole 216 and suspend the drill cuttings and solids while drilling is paused and/or when the drill bit 214 is brought in and out of the borehole 216.

At the surface, the recirculated or spent drilling fluid 222 exits the annulus 226 and may be conveyed to one or more solids control equipment 228 via an interconnecting flow line 230. In operation, the solids control equipment 228 may be configured to substantially remove the drill cuttings and solids from the drilling fluid 222 and deposit a "cleaned" drilling fluid 222 into a nearby retention pit 232 (i.e., a mud pit).

Several additives or components may be added to the drilling fluid 222 in order to maintain the drilling fluid 222 in proper working order and otherwise enhance drilling capabilities. In some embodiments, the additives and components may be added to the drilling fluid 222 via a mixing hopper 234 coupled to or otherwise in communication with the retention pit 232. In other embodiments, however, the additives and components may be added to the drilling fluid at any other location in the drilling assembly 200. In at least one embodiment, for example, there could be more than one retention pit 232, such as multiple retention pits 232 in series. Exemplary components that may be added to the drilling fluid 222 include, but are not limited to, emulsifiers, weighting materials, viscosifiers, thickeners, rheology modifiers, thinners, deflocculants, anionic poly electrolytes (e.g., acrylates, polyphosphates, lignosulfonates, tannic acid derivates, etc.), high-heat polymers, clay stabilizers, clay inhibitors, tar treatments, brine, dry salt(s), water and other base fluids, and combinations thereof. Exemplary weighting materials may include, but are not limited to, barium sulfate (i.e., $BaSO_4$ or barite), hematite, ilmenite, manganese tetraoxide, galena, calcium carbonate, or the like. Exemplary thickeners and/or rheology modifiers include, but are not limited to, xanthan gum, guar gum, glycol, carboxymethylcellulose, polyanionic cellulose (PAC), and starch, for example. Generally, exemplary components that may be added to the drilling fluid 222 will include any fluid additive, material, or component that is added to the drilling fluid 222 to change or maintain any preferred characteristic of the drilling fluid 222.

During drilling operations, concentrations of additive components have be established in the drilling fluid 222. The concentration of drilling fluid components may be continuously consumed or depleted from the drilling fluid 222 due primarily to being absorbed by generated drill solids. For example, components, such as emulsifiers, may be adsorbed onto the surfaces of drill solids which may include reactive clays, such as smectite, illite, and kaolinite. As the emulsifier component is progressively depleted from the drilling fluid 222 due to losses on drill cuttings and solids, the stability of the drilling fluid 222 emulsion may be impacted. As the drilling fluid 222 emulsion becomes unstable, the rheology of the drilling fluid may degrade and the wettability of the drilling fluid may be affected.

The wettability of drilling fluid 222 may be maintained in if the depletion rate of the components is counteracted with proper fluid treatment or management. Accordingly, knowing the wettability of the drilling fluids in real time may allow adjustments to be made to the concentration of drilling fluid components such that the wettability of the drilling fluid can be maintained. To accomplish this, one or more electrical meters 236 (shown as electrical meters 236 a, 236 b, 236 c, and 236 d) may be included in the drilling assembly 200 in order to monitor the drilling fluid 222 and/or one or more components present within the drilling fluid 222 at one or more monitoring locations. In some examples, one or more electrical meters 236 may be a conductivity sensor which may measure and report the real time characteristics of the drilling fluid 222, including ES voltage and/or wettability, which may provide an operator with real time data useful in adjusting various drilling parameters in order to optimize drilling operations and drilling fluid 222.

In an exemplary operation, the electrical meters 236 may measure and report the real time characteristics of the drilling fluid 222, including measured electrical properties of the drilling fluid using any of the techniques discussed herein including ES voltage. A wettability of the drilling fluid may be correlated from the measured electrical property which may provide an operator with real time data useful in adjusting various drilling parameters in order to optimize drilling operations and drilling fluid 222. One parameter which may be controlled is wettability.

In some examples, a first electrical meter 236 a may be arranged to monitor the drilling fluid 222 as it is recirculated or otherwise exits out of the borehole 216. As illustrated, the first electrical meter 236 a may be arranged on or otherwise coupled to the flow line 230, thereby being able to monitor the drilling fluid 222 once it exits the annulus 226. If initial concentrations or amounts of components were known prior to conveying the drilling fluid 222 into the borehole 216, the first electrical meter 236 a may be useful in providing data about changes in wettability of drilling fluid 222 during the drilling operation. As discussed above, drill cuttings from subterranean formation 218 may change the composition of the drilling fluid by selective sorption of components of the drilling fluid thereby altering the drilling fluid's physical properties. The subterranean formation may include stratified layers which may have varying effects on the physical properties of the drilling fluid. These and other effects may be monitored in real time using the equipment configuration above.

In other examples, a second electrical meter 236 b may be arranged on or otherwise in optical communication with the retention pit 232. The second electrical meter 236 b may be configured to monitor the drilling fluid 222 after it has undergone one or more treatments in the solids control equipment 228, thereby providing a real time electrical signal and/or wettability of drilling fluid 222 after undergoing treatment in solids controls equipment 228. In some examples, the second electrical meter 236 b may also be configured to monitor the drilling fluid 222 in the retention pit 232 as additional additive components are being added or otherwise mixed into the drilling fluid 222 via the mixing hopper 234. For instance, the second electrical meter 236 b may be able to report to an operator the effect on wettability when a particular additive component has been added to the drilling fluid 222. As will be appreciated, such real time measurement avoids unnecessarily overtreating the drilling fluid 222, thereby potentially saving time and costs.

In another example, a third electrical meter 436 c may be arranged in the drilling assembly 200 following the retention pit 232, but prior to the mud pump 220. Alternatively, or in addition thereto, a fourth electrical meter 436 d may be arranged in the drilling assembly 200 following the mud pump 220, such as being arranged at some point along the feed pipe 224. The third and/or fourth electrical meters 236 c, d may be useful in confirming whether adequate amounts or concentrations of components have been added to the drilling fluid 222 and otherwise determine whether the drilling fluid 222 has the correct wettability for adequate drilling operations. In other examples, the third and/or fourth electrical meters 236 c, d may be useful in providing an initial reading of characteristics of the drilling fluid 222, including concentrations of any components found therein, prior to the drilling fluid 222 being conveyed into the borehole 216. Such an initial reading may be compared with the resulting signal provided by the first electrical meter 236 a such that a determination of how the wettability of the drilling fluid is changed after circulation through the borehole 216.

In an example, one or more of the electrical meters 236 a-d may be communicably coupled to a signal processor 238 and configured to convey a corresponding output signal 240 a-d to the signal processor 238. The signal processor 238 may be a computer including a processor and a machine-readable storage medium having instructions stored thereon which may include instructions to correlate the output signal 240 a-d to a wettability, for example. Output signal 240 a-d may include a raw data output from the corresponding electrical meter such as the measured current or voltage, for example, or may be the ES voltage as determined by the ES meter circuitry, for example. The signal processor 238 may employ an algorithm configured to calculate or otherwise determine any differences between any two or more of the output signals 440 a-d. For example, the first output signal 440 a may be indicative of a wettability of the drilling fluid 222 exiting borehole 216 at the location of the first electrical meter 436 a, the second output signal 440 b may be indicative of the wettability of the drilling fluid 222 at the location of the second electrical meter 236 b, and so on. Accordingly, the signal processor 238 may be configured to determine if the wettability at one or more of the electrical meter locations is within predetermined limits such as water-wet, intermediate wettability, or oil-wet. The signal processor 238 may be further configured to output a signal to equipment configured to add chemical additives described above to the drilling fluid 222 to adjust the wettability.

As mentioned above, measuring an electrical property of a direct emulsion drilling fluid and correlating a result thereof to wettability may allow for interventions and treatments to the drilling fluid before the wettability causes process upset in the drilling operation. For example, the direct emulsion drilling fluid may be monitored using electrical meters at any of the locations in FIG. 2 and results of measurements may be correlated to wettability thereby providing real-time fluid monitoring. A requirement for intervention may be triggered when a wettability is detected that is above or below a setpoint. For example, when using the ES meter as described above, an arbitrary setpoint of 10 volts may be used as the threshold for upper limit of water-wet, 10 volts to 20 volts may be used as the threshold for intermediate wetness, and 20 volts and above may be used as the threshold for oil-wet. The setpoint for each wetness condition may depend on many factors, including the type of electrical testing equipment used.

Although the above discussion is focused on land-based operations, the method, apparatus, and systems described above may be readily adapted to offshore applications. For example, conductivity sensors may be placed within a mudline, a blow out preventer (BOP) stack, and/or throughout a riser which may afford additional monitoring of fluid conditions before reaching an offshore platform or other offshore rig.

Direct emulsion fluids with water-wet signals may indicate that the drilling fluid is in all clear state and drilling operations can continue. Intermediate signals may serve as alert for manual or automatic treatment intervention sequences. Treatments may include addition of a surfactant or other chemical additions to make the direct emulsion drilling fluid more water wet. Another treatment may be to direct the drilling fluid to a shear tank whereby a shearing force is applied to the drilling fluid. Shearing the drilling fluid may cause the wettability of the fluid to change to more water wet. In further examples, both chemical additives and shearing may be applied to the drilling fluid. Additional electrical meters may monitor the drilling fluid after chemical additive addition and/or shear to measure the effect on wettability the chemical additives and shear had on wettability. If the intervention with shear and/or chemicals is unsuccessful in changing the wettability of the drilling fluid, the volume of drilling fluid may be redirected to waste or holding tanks. Signals indicating that the direct emulsion drilling fluid is oil-wet may require treatment as with the intermediate signals or may require diversion of the drilling fluid to waste or storage such that the entire fluid circuit is not contaminated with oil-wet drilling fluid.

The methods described herein may also be used to detect tracers and wellbore or surface influx to drilling fluids. For example, a volume of drilling fluid with altered wettability, may be introduced into the wellbore or other portion of the fluid circuit. The altered wettability may be detected using the electrical testing equipment such that the volume of drilling fluid can be detected as it moves through the fluid circuit. Tracing volumes may be useful to define flow paths through the subterranean formation and to calculate surface circulation volume. Engineering calculations are often approximations based on ideal geometries and may have less accurate results than calculating circulation volumes by tracing a fluid through the fluid circuit. These calculations may be use to improve wellbore hydraulics models where wellbore washout can affect annular clearances. Further, the methods described herein may be used to detect and quantify influx of crude oil, formation water, fracturing fluids from neighboring wells, and rainfall surface contamination for example. These fluids may alter signals produced by the electrical test equipment which may then be detected and quantified which may allow for greater control with the fluid system. Interventions may be executed to improve fluid treatments as discussed above.

The methods described herein may also be utilized to determine when a fluid volume has been displaced from a wellbore. Some methods may estimate displacement from circulation and the wellbore volume. For example, when changing or displacing the well from a water-based fluid (A) to an oil-based fluid (B), the estimated pump strokes would be calculated for when A would push B out of the wellbore. In practice, an interface (C) between A/B will be formed, and the actual fluid returns will include of A-C-B. By using electrical testing equipment at the flowline, a response may be registered which may indicate a C and B have been displaced. The method proposed may allow for greater control of this process and increased efficiency in separating the fluid sets. Fluid C is typically treated as waste for most operations, so by reducing its volume the operation may achieve waste reduction and cost savings, as well improvement in quality of both A and B by minimizing influx/mixing. Additional control may be executed by manual or automatic valves to divert volumes to desired locations for efficient operations. For offshore operations, fluid A may often be discharged to the sea, and when C and A return to surface the circulation is shut down to reconfigure return flow conduits. By utilizing the signal response method and appropriate diversion of flow, circulation could be continued without need to cease for these activities. In a similar method, cleaning out wellbores containing B for completion involves a staged approach to flipping the formation wettability to water-wet with various spacer surfactants and A. Fluid designs are generally based on hydrodynamic models and wellbore volumes with specific spacers employed. Fluid parameters may be controlled to ensure an efficient and quick transition from B to C to A to minimize waste, cost and volume handling requirements. With distributed electrical signals indicating wettability changes through the fluid circuit, greater fluid efficiency may be achieved and the actual transition times may be used to further optimize modeling and planning for future cleanout operations. Sensors near the reservoir may also provide additional insight to the success of cleanout programs, and allow for remedial treatments if necessary.

Accordingly, the present disclosure may provide methods, systems, and apparatus that may relate to correlating electrical signals such as current or ES voltage to wettability. The methods, systems, and apparatus may include any of the various features disclosed herein, including one or more of the following statements.

Statement 1. A method of determining wettability comprising: measuring an electrical property of a drilling fluid; and correlating the electrical property to wettability.

Statement 2. The method of statement 1 wherein the electrical property is ES voltage and the step of measuring includes measuring using an ES meter.

Statement 3. The method of statement 2 wherein the step of correlating includes comparing the ES voltage to a calibration curve.

Statement 4. The method of statement 2 wherein the step of measuring includes: selecting a breakdown current; passing a ramping AC current through a first electrode in electrical communication with the drilling fluid; measuring a transmitted current at a second electrode in electrical communication with the drilling fluid; and determining the ES voltage by comparing the transmitted current to the breakdown current.

Statement 5. The method of statement 4 wherein the breakdown current is between about 1 µA to about 1000 µA.

Statement 6. The method of any of statements 1-5 wherein the drilling fluid is a direct emulsion drilling fluid.

Statement 7. The method of any of statements 1-6 further comprising obtaining the drilling fluid from a wellbore drilling operation.

Statement 8. The method of statement 7 wherein the obtaining includes obtaining the drilling fluid before the drilling fluid enters a drill string.

Statement 9. The method of statement 7 wherein the obtaining includes obtaining the drilling fluid after the drilling fluid exits a wellbore.

Statement 10. A system comprising: a conduit fluidically coupled to a wellbore and configured to receive a drilling fluid from the wellbore; an ES meter comprising electrodes in electrical communication with the drilling fluid; a signal processor communicably coupled to the ES meter configured to receive an output signal from the ES meter and correlate the output signal to wettability of the drilling fluid.

Statement 11. The system of statement 10 wherein the conduit is at least one of a conduit fluidically coupled to a wellbore annulus, a conduit fluidically coupled to a retention pit, a conduit fluidically coupled to a mud pump, or a feed pipe fluidically coupled to a drill string.

Statement 12. The system of statement 11 wherein the ES meter is configured to measure a current transmitted through the drilling fluid.

Statement 13. The system of any of statements 10-12 wherein the ES meter is configured to provide a ramping AC current through the drilling fluid.

Statement 14. The system of any of statements 10-13 wherein the ES meter is configured to output an ES voltage of the drilling fluid.

Statement 15. The system of any of statements 10-14 wherein the signal processor includes a computer including a processor and a machine-readable storage medium having instructions stored thereon which include instructions to correlate the output signal to a wettability.

Statement 16. A method comprising: conveying a direct emulsion drilling fluid from a wellbore drilling operation to an ES meter; measuring an ES voltage of the direct emulsion drilling fluid; and correlating the ES voltage to a wettability.

Statement 17. The method of statement 16 wherein the step of conveying includes conveying the direct emulsion drilling fluid from at least one of a conduit fluidically coupled to a wellbore annulus, a conduit fluidically coupled to a retention pit, a conduit fluidically coupled to a mud pump, or a feed pipe fluidically coupled to a drill string.

Statement 18. The method of any of statements 16-17 wherein the step of measuring an ES voltage include: selecting a breakdown current; passing a ramping AC current the direct emulsion drilling fluid; measuring a transmitted current through the direct emulsion drilling fluid; and determining the ES voltage by comparing the transmitted current to the breakdown current.

Statement 19. The method of any of statements 16-18 wherein the step of correlating includes sending a signal representing the ES voltage to a signal processor comprising a computer including a processor and a machine-readable storage medium having instructions stored thereon which include instructions to correlate the ES voltage to a wettability Statement 20. The method of any of statements 16-19 wherein the step of correlating includes correlating based at least in part on a breakdown current and the ES voltage.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method of determining wettability of direct emulsion drilling fluid comprising: measuring an electrical stability (ES) voltage of the direct emulsion drilling fluid; determining if the measured ES voltage is below a threshold ES value corresponding to water wet direct emulsion drilling fluids; determining if the measured ES voltage is above a different threshold ES value corresponding to oil wet direct emulsion drilling fluids; and correlating the electrical stability voltage to wettability of the direct emulsion drilling fluid.

2. The method of claim 1 wherein the step of correlating comprises comparing the ES voltage to a calibration curve.

3. The method of claim 1 wherein the step of measuring comprises:
   selecting a breakdown current;
   passing a ramping AC current through a first electrode in electrical communication with the drilling fluid;
   measuring a transmitted current at a second electrode in electrical communication with the drilling fluid; and
   determining the ES voltage by comparing the transmitted current to the breakdown current.

4. The method of claim 3 wherein the breakdown current is between 1 µA to about 1000 µA.

5. The method of claim 1 wherein the drilling fluid is a direct emulsion drilling fluid.

6. The method of claim 1 further comprising obtaining the drilling fluid from a wellbore drilling operation.

7. The method of claim 6 wherein the obtaining comprises obtaining the drilling fluid before the drilling fluid enters a drill string.

8. The method of claim 6 wherein the obtaining comprises obtaining the drilling fluid after the drilling fluid exits a wellbore.

9. A system to determine wettability of direct emulsion drilling fluid comprising:
   a conduit fluidically coupled to a wellbore and configured to receive a drilling fluid from the wellbore;
   an electrical stability (ES) meter comprising electrodes in electrical communication with the drilling fluid; and
   a signal processor communicably coupled to the ES meter configured to receive an output signal comprising ES voltage from the ES meter, determine if the measured ES voltage is below a threshold ES value corresponding to water wet direct emulsion drilling fluids, determine if the measured ES voltage is above a different threshold ES value corresponding to oil wet direct emulsion drilling fluids, and correlate the output signal to wettability of the direct emulsion drilling fluid.

10. The system of claim 9 wherein the conduit is at least one of a conduit fluidically coupled to a wellbore annulus, a conduit fluidically coupled to a retention pit, a conduit fluidically coupled to a mud pump, or a feed pipe fluidically coupled to a drill string.

11. The system of claim 10 wherein the ES meter is configured to measure a current transmitted through the drilling fluid.

12. The system of claim 9 wherein the ES meter is configured to provide a ramping AC current through the drilling fluid.

13. The system of claim 9 wherein the ES meter is configured to output an ES voltage of the drilling fluid.

14. The system of claim 9 wherein the signal processor comprises a computer including a processor and a machine-readable storage medium having instructions stored thereon which include instructions to correlate the output signal to a wettability.

15. A method comprising:
   conveying a direct emulsion drilling fluid from a wellbore drilling operation to an electrical stability (ES) meter;
   measuring an ES voltage of the direct emulsion drilling fluid;
   determining if the measured ES voltage is below a threshold ES value corresponding to water wet direct emulsion drilling fluids;

determining if the measured ES voltage is above a different threshold ES value corresponding to oil wet direct emulsion drilling fluids; and correlating the ES voltage to a wettability of the direct emulsion drilling fluid.

16. The method of claim 15 wherein the step of conveying comprises conveying the direct emulsion drilling fluid from at least one of a conduit fluidically coupled to a wellbore annulus, a conduit fluidically coupled to a retention pit, a conduit fluidically coupled to a mud pump, or a feed pipe fluidically coupled to a drill string.

17. The method of claim 15 wherein the step of measuring an ES voltage comprise:

selecting a breakdown current;

passing a ramping AC current the direct emulsion drilling fluid;

measuring a transmitted current through the direct emulsion drilling fluid; and determining the ES voltage by comparing the transmitted current to the breakdown current.

18. The method of claim 15 wherein the step of correlating comprises sending a signal representing the ES voltage to a signal processor comprising a computer including a processor and a machine-readable storage medium having instructions stored thereon which include instructions to correlate the ES voltage to a wettability.

19. The method of claim 15 wherein the step of correlating comprises correlating based at least in part on a breakdown current and the ES voltage.

* * * * *